United States Patent [19]

Kuntz et al.

[11] Patent Number: 5,522,823
[45] Date of Patent: Jun. 4, 1996

[54] CLIP FOR SURGICAL USE AND CLIP APPLICATOR

[75] Inventors: Bertram Kuntz, Steinfeld; Karl Schlipf, Karlsruhe; Heinrich Schülken, Stutensee-Staffort, all of Germany

[73] Assignee: Kernforschungszentrum Karlsruhe GmbH, Karlsruhe, Germany

[63] Continuation-in-part of PCT/EP93/01929

[21] Appl. No.: 352,904

[22] Filed: Dec. 9, 1994

[30] Foreign Application Priority Data

Sep. 9, 1992 [DE] Germany .............. 42 30 102.5

[51] Int. Cl.$^6$ .................................... A61B 17/04
[52] U.S. Cl. ................. 606/157; 606/142; 606/158; 606/151
[58] Field of Search ................... 606/142, 143, 606/151, 157, 158

[56] References Cited

U.S. PATENT DOCUMENTS

| 4,325,377 | 4/1982 | Boebel | 606/142 |
| 4,487,204 | 12/1984 | Hrouda | 606/142 |
| 4,556,060 | 12/1985 | Perlin | . |
| 5,449,365 | 9/1995 | Green et al. | 606/142 |
| 5,462,558 | 10/1995 | Kolesa et al. | 606/142 |

Primary Examiner—Gary Jackson
Attorney, Agent, or Firm—Klaus J. Bach

[57] ABSTRACT

A clip for use in surgery which comprises a lower and an upper portion interconnected by a flexible bridge portion wherein the lower clip portion has at its free end a pin with pointed end extending toward the upper clip portion and the upper clip portion has at its free end a rounded protector nose and has, adjacent thereto, an opening adapted to receive and engage the pin when the upper and lower clip portions are pressed together and the bridge portion is deformable at two points essentially at right angles such that, upon final deformation of the bridge portion, with the clip closed the lower and upper clip portions extend essentially parallel and are, at the bridge portion closer together than they are by simply closing the clip before the final deformation of the bridge portion.

7 Claims, 5 Drawing Sheets

Fig. 1A
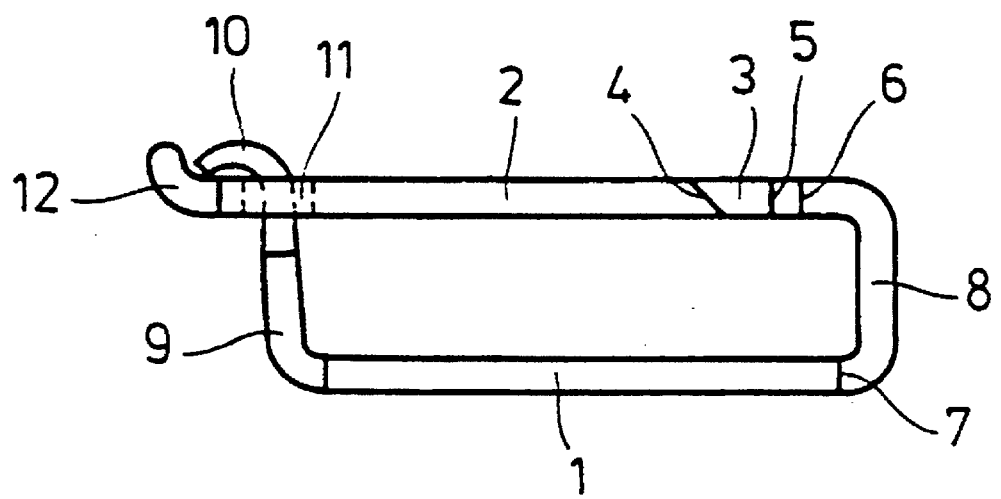
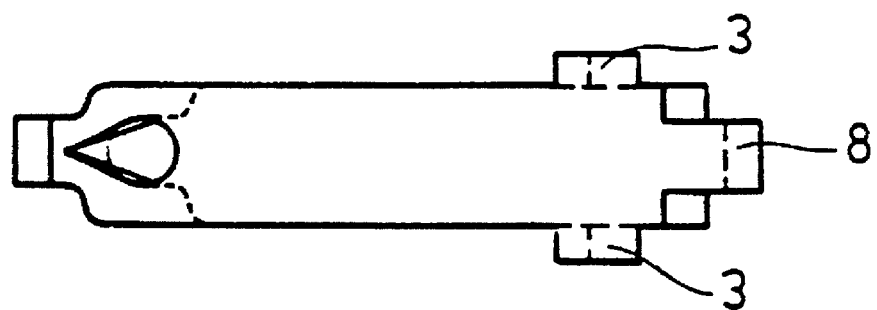
Fig 1B

CLIP FOR SURGICAL USE AND CLIP APPLICATOR

This is a continuation-in-part application of International application PCT/EP93/01929 claiming priority of German application P 42 30 102.5 of Sep. 9, 1992.

BACKGROUND OF THE INVENTION

The invention relates to a clip for use in surgical procedures and an apparatus for fitting the clip.

In the medical field a plurality of clips of various shapes are known as well as apparatus for fitting the clips. Such a clip is disclosed, for example, in U.S. Pat. No. 4,498,476. The clip described therein which serves for clamping off blood vessels consists of an upper clip portion and a lower clip portion which are interconnected symmetrically by a resiliently flexible bridge portion. At the end opposite the bridge portion the upper clip portion is provided with an opening adapted to catch a pin projecting from the lower clip portion. In some embodiments the pin is provided with a roof- or arrow-like point. The pin and the point cooperate with the opening to serve as locking elements for closing the pin. In the closed position of the clip the upper and lower portions of the clip are in contact with one another. However, the edges of tissue cannot be engaged by such a clip.

DE 30 34 356 A1 discloses a surgical clamp particularly for clamping blood vessels which also consists of an upper and a lower part which are interconnected symmetrically by a resiliently flexible bridge structure. The upper portion has an opening formed therein at the end opposite the bridge structure and a ratchet projecting from the lower portion is adapted to be received in the opening. At one side the ratchet is provided with teeth by means of which the clamp can be closed and locked. But also with this clamp, edges of tissue cannot be engaged.

In German UM G 83 29 725 a microclip for medical applications is described which consists of an elastically deformable material and which comprises a U-shaped member with portions extending from the free ends of the legs of the U backward to the center of the U in parallel linear relation with the legs and which are characterized in that the parallel portions are disposed at a small distance from the legs of the U and are in contact with the legs only near their point of connection with the free legs of the U. The microclip preferably consists of soft elastic stainless steel. The free ends of the U-shaped member may have openings for engagement by a clip handling instrument. This microclip is also designed mainly for clamping blood vessels. For the engagement of the edges of tissue after surgical incisions it appears to be not particularly suitable.

A further surgical microclip is described in EP 04 32 743 A1. This microclip includes two oppositely disposed flanges of sheet metal. The flanges have at one end edge portions with pointed projections directed toward one another and, at the opposite end, they have operating areas which can be compressed against the force of a spring. The microclip is formed as a one-piece structure and includes a resiliently elastic connecting flange disposed between the operating areas.

Since this microclip is apparently to be mounted by hand it needs to be relatively large and, therefore, is not suitable for internal surgery and particularly not for minimally invasive surgery.

DE 31 39 488 C2 discloses an aneurysm-clip which comprises two legs which are pivotally joined to, and cross, one another and which serve to fix tissue. The legs are compressed by a double-coiled spring wire which is connected to both legs.

A similar clip is disclosed in DE 35 23 031 A1. In this clip the double-coil spring wire is replaced by a hub comprising two hub sections which are joined by a pin so as to be rotatable relative to one another.

The two last-mentioned clips are suitable particularly for the temporary pinching of blood vessels; they are not suitable for the permanent fixing of tissue edges after incisions.

DE 30 28 259 A1 discloses a tube litigation pistol by which clips for the interruption of vessels can be mounted. The apparatus is suitable for clips whose upper and lower portions are mounted on an axis so as to be pivotal relative to one another and which can be fixed by a spring.

A clip mounting plier is known from DE 40 24 636 A1. This clip mounting plier comprises a tube which is axially movable by means of two handle halves. At the distal end of the tube there are two jaws which can be closed or opened by a rope extending through the tube. The tube consists of a hose-like elastic sleeve which remains in position during movement of the rope. The clip mounting plier obviously serves for the mounting of aneurysm clips.

A further plier for mounting of a styptic clamp is described in DE 40 15 562 A1. This plier is provided at its distal end with two jaws which are operable by operating handles at the proximal end via an operating rod extending through a tube. The operating rod is hollow and serves as a magazine for receiving a number of clips. However this plier is designed for mounting only U-shaped clips.

It is the object of the present invention to provide a clip and a clip applicator for mounting such a clip by means of which, during minimal invasive surgery, after lesions and incisions the edges of tissue can be placed together and fixed through an access sleeve.

SUMMARY OF THE INVENTION

A clip for use in surgery which comprises a lower and an upper portion interconnected by a flexible bridge portion wherein the lower clip portion has at its free end a pin with pointed end extending toward the upper clip portion and the upper clip portion has at its free end a rounded protector nose and has, adjacent thereto, an opening adapted to receive and engage the pin when the upper and lower clip portions are pressed together and the bridge portion is deformable at two points essentially at right angles such that, upon final deformation of the bridge portion, with the clip closed the lower and upper clip portions extend essentially parallel and are, at the bridge portion closer together than they are by simply closing the clip before the final deformation of the bridge portion.

Advantageous embodiments of the invention are defined in the dependent claims.

BRIEF DESCRIPTION OF THE DRAWINGS

FIG. 1A is a side view of the clip according to the invention in closed position;

FIG. 1B is a top view of the clip;

FIG. 6A is an enlarged representation of the distal end of the applicator;

DESCRIPTION OF THE PREFERRED EMBODIMENT

Figure 2:
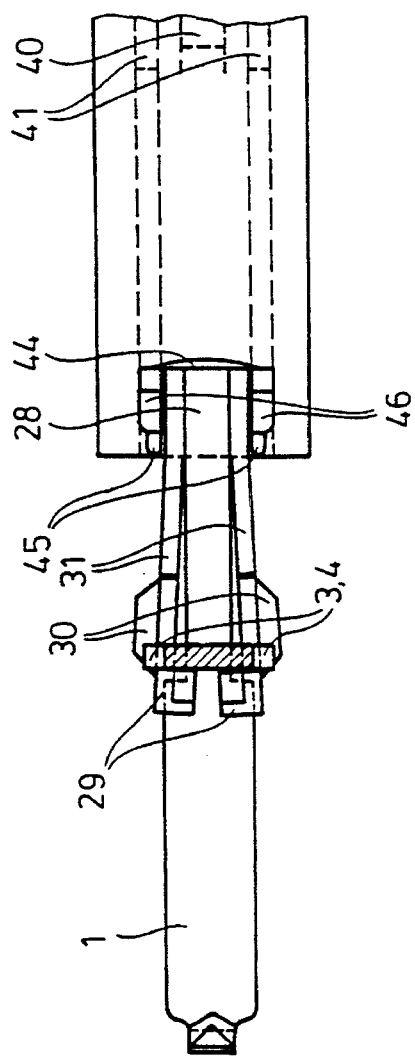
FIG. 2 is a top view of the distal end of an applicator with a clip engaged thereby.

FIGS. 1A and 1B show the clip according to the invention in its tissue engaging final shape. It consists of a lower clip portion 1 and an open clip portion 2 which are interconnected by a flexible bridge portion 8.

The clip may consist all together of a suitable bendable material such as a stainless steel wire of uniform cross-section. Upon mounting of the clip, the bridge portion is deformed by a correspondingly designed applicator whereas the lower clip portion retains its shape. Preferably, the cross-section of the bridge portion is smaller than that of the other portions of the clip. In this manner, a large force can be applied by the pin 9 to the tissue during mounting without being bent whereas the force required for the bending of the bridge portion 8 is quite limited.

The clip according to the invention has a plane of symmetry. The lower portion 1 of the clip is provided at its free end with a pin 9 which is angled upwardly in the plane of symmetry and has a pointed end 10. The upper clip portion 2 is provided at its free end with a rounded protective nose 12. Adjacent the protective nose the upper clip portion 2 has an opening 11 which is disposed in the plane of symmetry. The lengths of the lower clip portion 1 with the pin 9, the soft flexible bridge portion 8 and the upper clip portion 2 up to the opening 11 are so selected that the pin 9 with its pointed end 10 is received in the opening 11 when the upper clip portion 2 is pressed toward the lower clip portion 1 while the bridge portion 8 is bent.

With the pointed end 10 of the pin 9 the tissue to be held together and to be position-fixed is pierced and engaged. Then the upper clip portion 2 is pressed onto the pin 9 of the lower clip portion 1 by bending of the bridge portion 8 until the pointed end 10 extends through the opening 11. The cross-section of the pointed end 10 of the pin and the cross-section of the opening 11 are selected so as to accommodate one another. The most simple solution resides in a circular opening 11 and a conically or pyramidically shaped pointed end 10.

Preferably the protective nose 12 is bent-over in the same direction as the pin 9. With this arrangement the clip is safe from being opened unintentionally and, at the same time, the pin end 10 is retained in such a way that further injuries to the fixed tissue are avoided. For this purpose, the end 10 of the pin projecting from the opening 11 is bent over onto the protective nose 12 such that it is protected by the protective nose 12.

The design of a suitable applicator is facilitated if the bridge portion 8 of the clip has a relatively small cross-section and if engagement surfaces 6, 7 are provided on the upper clip portion 2 and the lower clip portion 1 in the interface area between these clip portions and the bridge portion 8. It is further advantageous if the upper clip portion 2 is provided with projections 3 extending therefrom adjacent the bridge portion 8 in opposite directions perpendicularly to the plane of symmetry of the clip. It is particularly advantageous if the projections have inclined side surfaces 4 at their side remote from the bridge portion 8.

Figure 3:
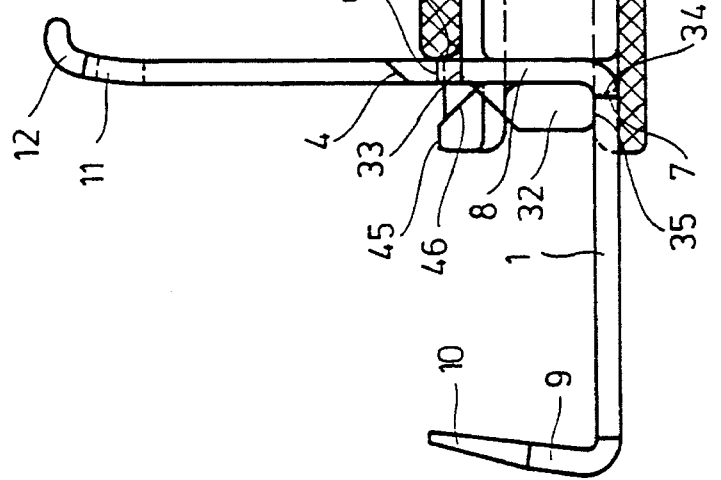
FIG. 3 is a side view of the distal end of an applicator with a clip first engaged thereby.

The clip according to the invention may be punched from sheet metal and may then be bent into the shape as shown in FIG. 3. It comprises a single part so that assembly of small parts is not necessary. With a suitable selection of material such as smoothly flexible stainless steel the bridge portion can be bent several times without breakage. The clip may be so small that it can be moved through commonly used operating sleeves of 5, 7 or 10 mm diameter.

Figure 6:
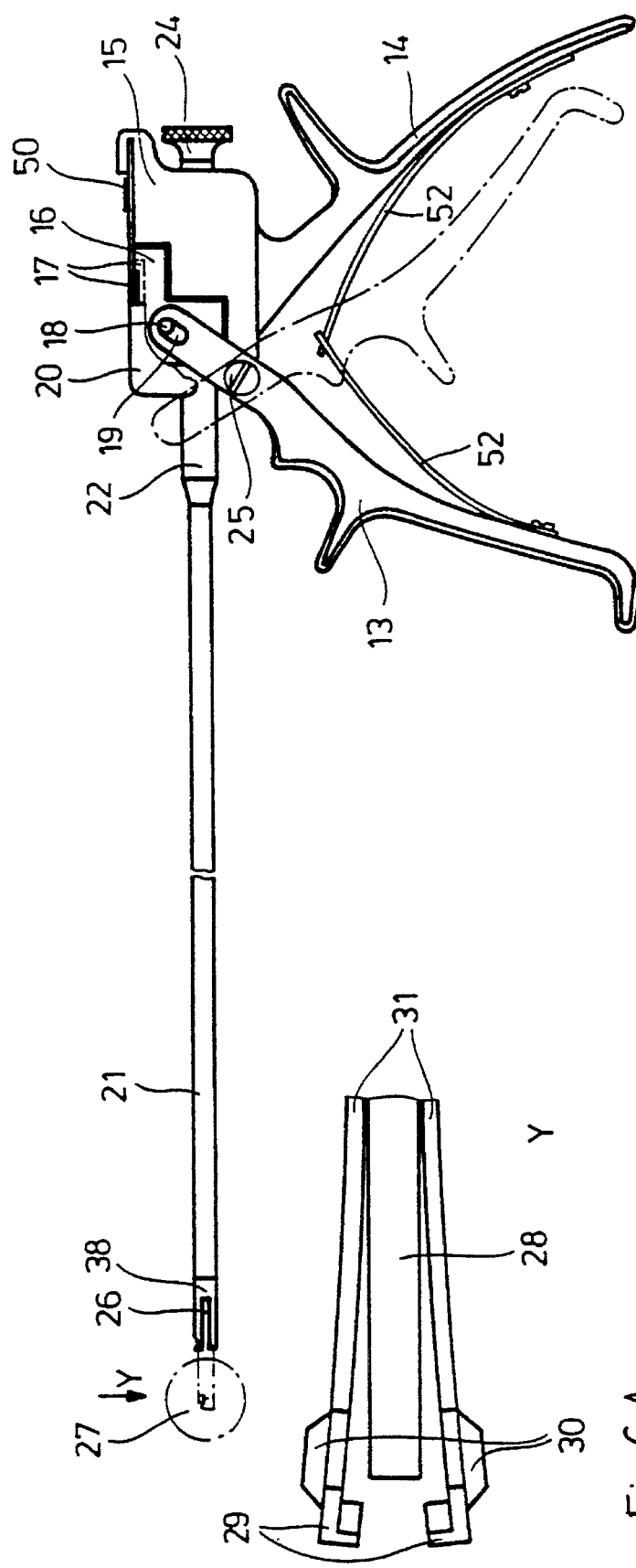
FIG. 6 is a side view of the whole applicator.

The design of an applicator adapted to be the clip according to the invention is best apparent from FIGS. 3 and 6. It comprises the following essential features:

a) a clip holder for grasping and engaging the flexible bridge portion 8 of the clip;

b) an applicator tube 39 which, by means of operating handles 13, 14, is movable axially and vertically with respect to bridge portion 8 of the clip engaged thereby and whose head 38, upon advancement thereof, deforms the clip in the area of its flexible bridge portion in such a way that the lower clip portion 1 and the upper clip portion 2 assume an essentially parallel position;

c) two opening studs 47 in the applicator head 38 and a stop bar 28 in the clip holder 27 by means of which, upon back-up movement of the applicator tube 39, the upper clip portion 2 can be moved to an essentially normal position with respect to the lower clip portion 1.

Figure 4:
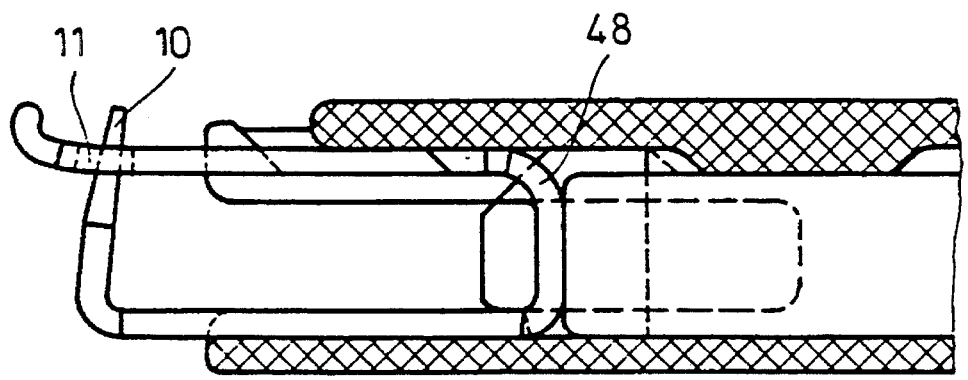
FIG. 4 is a side view of the distal end of an applicator with a clip deformed so as to be movable into an access sleeve.

The embodiment of the clip applicator as shown in FIGS. 2 to 8 is designed for single-hand operation. It permits insertion of the clip in the form as shown in FIG. 4 by means of an access sleeve of 5, 7 or 10 mm diameter as adapted to the applicator head 38 and the applicator tube 21.

Figure 5:
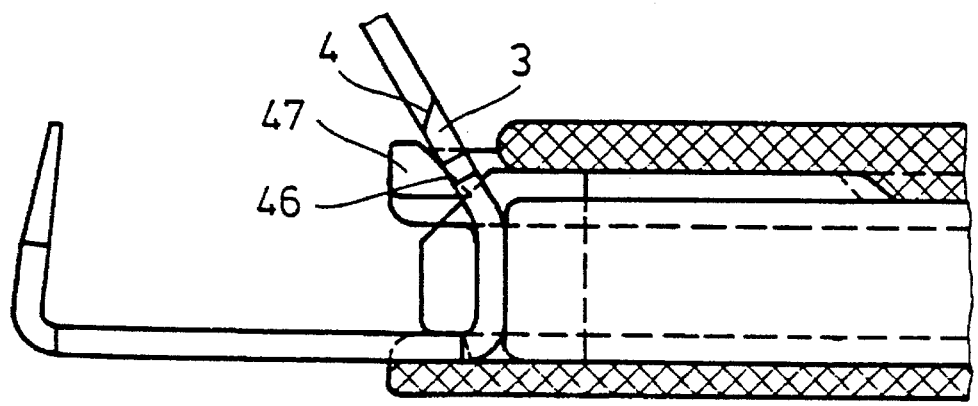
FIG. 5 is a side view of the distal end of an applicator with a partially opened clip ready for application.
Figure 7:
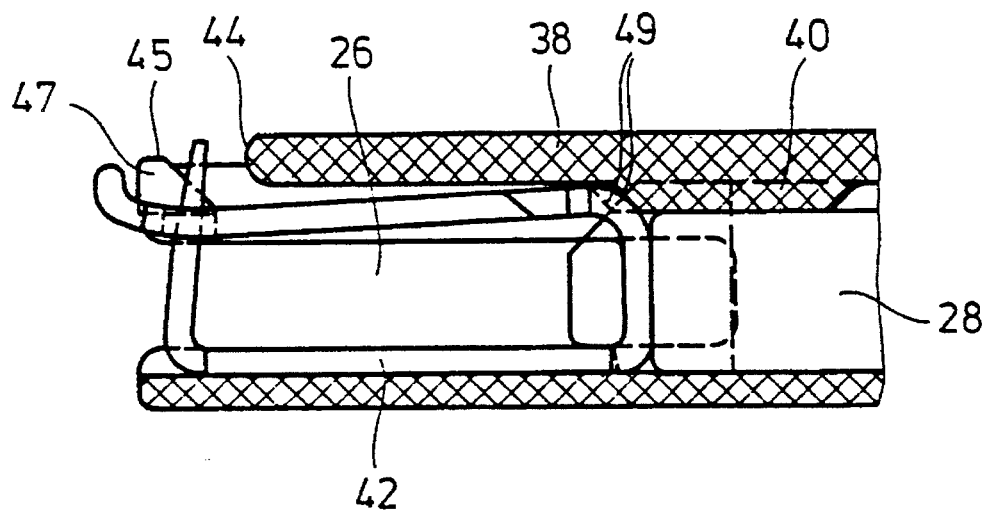
FIG. 7 shows the distal end of the applicator and the deformed clip after engagement of tissue edges (which are not shown)
Figure 8:
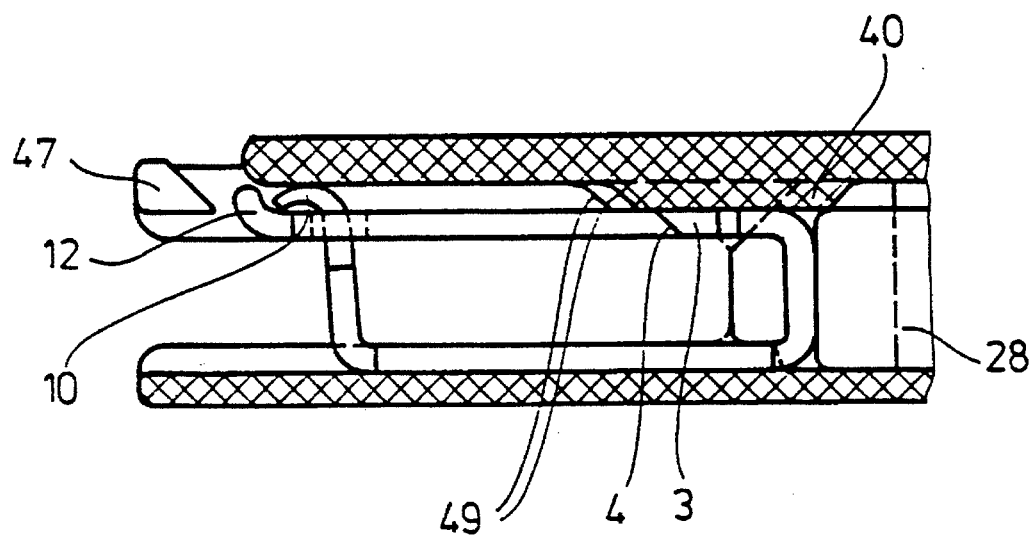
FIG. 8 shows the distal end of the applicator with a deformed clip which is secured against opening after engagement of the tissue (which is not shown).

Simply by translatory motion of the outer shaft portion which comprises parts 22, 38 and 39 relative to the inner shaft member 23 and to the clip holder 27, the clip is engaged in the manner as shown in FIG. 4 and is inserted into an access sleeve and is opened to the shape as shown in FIG. 5. After the tissue is placed together and onto the pin 9, the clip is closed as shown in FIG. 7 and then locked as shown in FIG. 8. The pin 9 is then released. The closing and opening of the pin 9 is achieved by deforming the hinge portion 48 (FIG. 4) at the bridge portion 8 by means of the force pair effective between the holder boss 32 and the stop and forming structure 44 which is engaged by the pin 9 when the applicator tube 39 is moved toward the distal end of the applicator for closing the clip; or, respectively, the force pair generated between the stop bar 28 and the opening stud 47 during retraction of the applicator tube for opening the clip.

The clip applicator and the clip are so adapted to one another that, in accordance with FIG. 3, the backside 5 of the projection 3 of the upper clip portion can be moved over the top surface 45 of the opening studs 47 on the applicator head 38 up to the stop and forming structure 4 with sufficient clearance.

During opening and closing the clip moves in translatory respect about between the position as shown in FIG. 5 and the front end of the final forming structures 40 and 41 in the applicator head 38 (see FIG. 3). By the design of the applicator head 38 and the clip holder 27, the radius of the hinge structure 48 is relatively large and its plastic deformation will lead to material failures only after an unrealistically large number of operations.

Upon opening of the clip the force pair described above becomes effective on the bridge portion 8 and the two projections 3 on the upper portion of the clip which results in an increase of the radius of curvature of the hinge structure 48.

After being engaged and retracted into the applicator head as shown in FIG. 3, the clip is securely held and/or guided by engagement with the following holding or guide surfaces:

between the distal surface of the stop bar 28 and the holder boss 32, by the engagement surface 7 on the lower clip portion and the lower indexing surfaces 34 of the holder heads 29, by the engagement surface 6 on the upper clip portion 2 and the indexing surfaces 35 on the holder heads 29, by the guidance of the lower portion 1 at the side thereof in the guide groove 42 of the applicator head 38 as well as, in a direction normal thereto, the guidance between the underside of the holder bosses 32 and the bottom surface of the guide groove 42, by the side engagement of the bridge portion 8 in the holder heads 29, by the (transient) side guidance of the upper clip portion 2 between the opening studs 47 of the applicator head 38, by the sliding engagement of the upper clip portion 2 with the bottom surface of the guide groove 51 in the applicator head 38, and by the side support of the clip projections 3 on the upper clip portion 2 in the guide groove 51 of the applicator head 38.

Sideward movement and opening of the holder heads 29 in the guide groove 51 as a result of the clip engagement forces is prevented by the support provided for the holder heads by the side surfaces of the guide groove 51 via the guide ribs 30.

The clip holder 27 and, consequently, also the clip engaged thereby, can be controlled accurately via the inner shaft member 23 and the stationary handle part 14 by the hand of an operator in an ergonomically advantageous manner. The closing and the opening of the clip during surgery by slide movements of the applicator head 38 and the applicator tube 39 by actuation of the finger-operated handle part 13 does not result in dislocation of the clip which movement would have to be counteracted by the operator.

The operating sequence when following the above operating system functions as well as the necessary movements of the applicator head 38 relative to the clip holder 27 are predetermined by the guide tracks 17 in the operating head 16 which are engaged by a tongue mounted on spring lever 20 which is pivotally mounted on the handle housing 15 and which is movable by the thumb toward the handle housing 15 against the force of the leaf spring 50 for exchanging the guide tracks 17.

Three operating ranges are provided by this program mechanism:

Range 1: Holding and loading of the clip.

The applicator head 38 is brought from the position shown in FIG. 6 to the position shown in FIG. 5 relative to the clip holder 27 by actuation of the finger-operated handle part 13. The handle part 13 is then locked so that its return by the leaf springs 52 to its original position is prevented.

Range 2: Closing and opening of the clip.

By means of the finger-operated handle part 13 the applicator head 38 can be moved relative to the clip holder 27 back and forth between two end points given by the guide tracks 17. Upon backward movement the clip is opened (FIG. 5) for receiving tissue edges and upon forward movement the clip is closed (FIG. 4). Unintentional release or locking of the clip is not possible.

Range 3: Locking and releasing of the clip.

After placement of both tissue edges onto the pin 9 of the clip, the spring lever 20 is actuated by the thumb of the operator as described earlier. Then, the tongue of the spring lever 20 snaps into a lower second portion of the guide tracks 17 which permits further movement of the finger-operated handle portion 13 whereby, with the actual and outer final forming structures 40 and 41, the hinge structure 48 is deformed such that the upper clip portion 2 is moved downwardly (FIGS. 7, 8) onto the lower clip portion 1 and finally the pin end 10 is bent-over onto the protector nose 12 such that the clip is locked (FIG. 8). Upon release of the finger-operated handle part 13 the applicator head 38 is retracted by the force of the leaf springs 52 and the clip is released with the tissue edges fixed by the clip.

Upon release and removal of the coupling bolt 18 which engages the finger-operated handle with the operator head and of the knurled screw 24, the applicator shaft 21 including the applicator head 38, the clip holder 27 and the operating head 16 with the guide tracks 17 can be exchanged. It is advantageous that, with this design, the applicator head and the operating head are exchanged together so that the guide tracks are necessarily also exchanged for proper replacement by the equipment needed for handling clip of different sizes.

As usual for the known tie clips the present system also comprises the clip and the corresponding applicator.

Also, like with the tie clips, for clips with pins the use of a multi-part clip set with clips of different sizes, depending on the particular application and the corresponding applicators or applicator heads, is proposed.

The operating mechanism as described permits handling of applicators with 5 mm, 7 mm and 10 mm outer shaft diameters disposed in suitable handling sleeves. A switch-over of the applicator shafts 21 is possible by operating the coupling bolt 18 in the operating head and the knurled screw 24 on the handle housing 15 which interconnects the handle housing 15 and the inner shaft member 23.

The applicator consists of three building components:

The applicator head 38 with the applicator mouth 26, the guide grooves 42, 43 and 51, the central and outer final forming structures 40, 41 and the opening studs 47 in connection with the clip holder 27 serve for receiving and controlling the clip.

The handle consists essentially of the stationary handle part 14, the finger-operated handle part 13, which is pivotally connected to the stationary handle part by a bolt 25, the leaf springs 52 for returning the finger-operated handle part, the handle housing 15 with the pivotable spring lever 20 and the leaf spring 50 for its return after actuation. The handle is designed for single-hand operation. It permits holding and guiding the applicator, operation of the applicator head 38 and the operation of the spring lever 20 by the thumb of the operator during the clip application procedure.

The applicator shaft 21 with the applicator tube 39, the transition part 22, the operating head 16 connected to the transition part 22 and the inner shaft member 23 represent the connecting structure between the applicator head 38 or the clip holder 27 and the handle and may have a length as desired for a particular application. The operating head 16 includes two guide tracks 17, which, in connection with a tongue of the spring lever 20, provide for a safe follow-up of the applicator operating procedure. The guide tracks 17, which are arranged side-by-side, guide the tongue of the spring lever 20 upon actuation of the applicator handle in different planes.

Following is a detailed description of the applicator operating procedure for the clip shown in FIG. 1.

Holding and Loading of the Clip

The open clip as shown in FIG. 3 is taken by the clip holder 27 from a suitable magazine or from a forceps. In the retracted end position of the applicator head 38 as shown in FIGS. 6, 6A, the clip holder is fully open. The clearance between the holder bosses 32 and the holder heads 29 is maximal in this position and is given by the outwardly bent unstressed position of the leaf springs 31.

When the bridge portion 8 of the pin abuts the distal end of the stop bar 28 the applicator head 38 can be moved in a distal direction. Then the clip holder 27 is closed as the applicator head 38 is moved forward relative to the holder heads 29. Upon reception of a clip from a magazine, it is made certain that the clip is accurately positioned with respect to the holder heads 29 such that the bridge portion 8 is positioned exactly between the adjacent surfaces of the holder bosses 32 and the distal end of the stop bar 28. It is then further made certain that the position of the clip in the holder heads 29 is fixed by its guidance by the engagement surfaces 7 of the lower clip portion 1, by the lower indexing surfaces 34 of holder heads 29 and by guidance of the engagement surfaces 6 of the upper clip portion 2 on the upper indexing surfaces 33. Since such accurate coordination of clip and clip holder is not automatically assured during remote handling, particular care must be taken during such operation.

After positioning of the clip in the open clip holder 27 the holder bosses 32 can be closed by advancing the applicator head 38 in distal direction as described.

At the end of the closing step the part of the upper clip portion 2 between the backside of the pin 5 and the engagement surface 6 and a part of the hinge structure 48 of the bridge portion 8 which is not yet bent, slides through the free space between the opening studs 47 on the applicator head 38. By design, there is provided a sufficient distance between the backside 5 of the projections 3 of the still upstanding upper clip portion 2 and the top surfaces 45 of the opening studs 47.

The guide ribs 30 of the holder heads 29 are also received in the guide groves 51 and prevent opening of the clip holder 27 under load by engagement of the holder heads between the walls of the guide grooves 51.

The guide ribs 30 pass underneath the opening studs 47 of the applicator head.

The holder heads 29 are then pulled together with the lower clip portion 1 into the lower guide groove 42 of the applicator head 38.

Until the upper clip portion 2 comes into contact with the stop and forming rib 44 of the applicator head 38, the clip shape remains unchanged as shown in FIG. 3.

Further advancement of the applicator head relative to the clip holder 27 causes deformation of the flexible bridge portion 8 in the area of the hinge structure 48 between the stop and forming rib 44 and the holder boss 32 in such a manner that the upper clip portion 2 is bent downwardly in closing direction toward the lower clip portion. The clip is then in the shape as shown in FIG. 5. However, the upper clip portion 2 is still in engagement with the stop and forming rib 44.

During the translatory applicator head movement as described so far, the tongue of the spring lever 20 follows the guide track 17 for position determination of the applicator head. FIG. 3 shows the open clip position. After initial slight deformation, the bridge portion 8 has the shape as shown in FIG. 5.

Then the loading step for the applicator is completed. The finger-operated handle part 13 is secured against return to its original position by blocking the operating head 16. An unintentional release of the clip is therefore prevented.

Closing and Opening of the Clip

When the applicator head 38 is moved from the loading position further in distal direction relative to the clip holder 27, the closing movement of the clip which was initiated at the end of the loading procedure is continued. The clip slides further into the guide grooves 42 and 51. The bridge portion 8 adjacent the upper clip portion 2 between the holder boss 32 and the stop and forming rib 44 becomes a hinge structure 48 by the force pair acting on the clip.

The projections 3 protruding sidewardly from the upper clip portion 2 extend through the gap between the opening studs 47 and the stop and forming rib 44 into the guide groove 51 and slide along the side surfaces thereof thereby providing side support for the upper clip portion 2. Additional side support is provided for the upper clip portion during the closing step by the side walls of the adjacent opening studs 47 of the applicator head 38 (FIGS. 3, 4).

The position of the clip as shown in FIG. 4 which remains unchanged during further advancement of the applicator head up to its contact with the ramp surfaces 49 of the final forming ribs 40 and 41, permits the insertion of the clip and the applicator head 38 through a corresponding operating sleeve in operating position, since the cross-section of the clip is now smaller than the outer contour of the applicator head.

The distal advancement length of the applicator head 38 relative to the clip holder 27 is limited by a stop for the spring lever tongue at the proximal end of the first guide track 17 in the operating head. Unintended locking of the clip by bypassing the final forming ribs 40 and 41 is therefore prevented. As long as the applicator head 38 is moved relative to the clip holder 27 within a range which is limited by distal and proximal stops of the first guide track 17 the clip remains secure from unintended release or locking.

For the grasping and engaging of the first tissue edge the clip has to be opened at the location of its application. For this purpose the finger-operated handle part is released and is returned by the leaf springs 52 between the handle parts, the leaf springs 52 being selected to be sufficiently strong for this task. The applicator head 38 is retracted thereby.

When the inclined surfaces 4 of the pins 3 of the upper clip portion 2 are engaged by the ramp surfaces 46 of the opening studs 47, a force component is generated by the separation of the pulling force parallel to the applicator axis, which force component acts on the projection 3 of the upper clip portion 2 such that the clip is opened by partial straightening of the hinge structure 48 as shown in FIG. 5.

The pointed end 10 of the pin 9 of the lower clip portion 1 is placed onto the outer surface (the surface which, without incision, would be adjacent the applicator) of the tissue adjacent the incision edge and by axial movement of the pin 9 the tissue is pierced. This can be supported by careful longitudinal movement of the applicator in proximal direction. Since the pin 9 is inclined backward toward the clip bridge portion, additional forces are created by such longitudinal applicator movement which facilitate the piercing of the tissue.

If the tissue cannot readily be pierced the applicator head 38 is moved relative to the clip holder in a distal direction by actuating the finger-operated handle part whereby the clip will be closed as described above.

Then the tissue disposed between the pointed pin end 10 and the opening 11 in the upper clip portion is easily pierced as it is engaged by the upper clip portion so that it cannot yield and the tissue edge is engaged by the pin 9. Upon closing of the clip the tissue edge disposed in the open cross-section of the clip is received in the mouth 26 of the applicator head 38.

Upon renewed opening of the clip the second tissue edge is pierced from the incision side or the backside of the tissue so that it is disposed on the pin 9. If the pin has to be closed to achieve piercing, the finger-operated handle part 13 can be pulled up to the stop of the spring tongue at the proximal end of the guide track 17.

In this handle and applicator head position the outside of the hinge structure 48 is disposed closely ahead of the ramp surfaces 49 of the final forming structures 40 and 41.

Then the loading and fixing of the tissue edges relative to one another is completed. Now it is necessary to lock the clip since, by its design with an easily flexible bridge portion, the clip is not capable of taking up the tissue fixing forces without locking as a normal bend-resistant tying clip would be.

Locking and Releasing the Fixed Clip

For the positive locking of the loaded clip after the clip is closed as shown in FIG. 4, the spring lever 20 is pressed with the thumb of the hand holding the handle toward the handle housing 15 against the force of the leaf spring 50. This causes the tongue of the spring lever 20 to a second guide track 17. After this short singular application of pressure to the spring lever 20, the tongue is captured in the guide track 17. It glides along between grooves of the guide track 17 and prevents the return of the spring lever 20 before the release of the clip.

Upon further movement of the finger-operated handle 13 whereby the applicator head 38 is further advanced in relation to the clip holder 27, the hinge structure 48 of the clip comes first in contact with the ramp surface 49 of the central and outer final forming structure 40 or 41.

If the tissue forces directed upwardly are not excessive, the distal end of the upper clip portion 2 moves, as shown in FIG. 7, further toward the lower clip portion 1 under deformation of the hinge structure 48 until the lower end of the rim around the opening 11 is seated on the inclined sides of the pointed end of the pin 10.

Upon further advancement of the applicator head 38, the hinge structure 48 is forced under the final forming structure 40 and 41 whereby the upper clip portion is brought to the shape as shown in FIG. 8.

This step also results in a distal displacement of the opening 11 in the upper clip portion relative to the bridge portion 8. Consequently also the pointed end of the pin which is received in the opening 11 is moved slightly outwardly in distal direction as shown in FIG. 8.

During reshaping of the hinge structure 48, also the pointed end of the pin 10 is bent-over by the stop and forming rib 44 and then is slidingly received in the guide groove 51.

The protector nose 12 at the end of the upper clip portion 2 is somewhat straightened out depending on the thickness and the resiliency of the tissue engaged by the clip. The return forces of the protector nose 12 after deformation insure that the bent over pin end 10 is abutted by the protector nose as the upper clip portion was supported on the pin edges during bending of the hinge structure 48 so that damage to the tissue is prevented.

The deformations described so far are achieved by moving the applicator head 38 and the applicator tube 39 up to the stop of the tongue of the spring lever 20 at the proximal end of the guide track 17.

The upper clip portion 2 has been moved further toward the axis of the applicator mouth 26 (FIG. 8) by the deforming and the closing steps because of the guide groove 51 in which the opening and closing of the clip was achieved by translational sliding. The projections 3 on the upper clip portion are now disposed, as shown in FIG. 8, in a plane beneath the opening studs 47. If the applicator head 38 is now pulled back in proximal direction the projections 3 of the upper clip portion are passing below the opening stud 47.

After further retraction of the applicator head 38 the leaf springs 31 open the holder heads 29 which engage the clip bridge portion 8 so that the holder bosses 32 release the clip in a shape as shown in FIG. 1, but with the tissue edges engaged thereby.

Toward the end of the releasing procedure the tongue of the spring lever 20 jumps, under the pressure of the leaf spring 50, back to first guide track 17. Then the spring lever 20 is again in its original position.

The applicator with the projecting clip holder 27 can be removed from the operation location through the handling sleeve and can be loaded immediately with the next clip.

What is claimed is:

1. A clip for use in surgery, comprising a lower clip portion and an upper clip portion, and a flexible bridge portion interconnecting said lower and upper clip portions, said lower clip portion, said upper clip portion and said flexible bridge portion being disposed in a plane of symmetry, said lower clip portion having at its free end opposite said bridge portion a pin angled therefrom so as to extend in said plane of symmetry toward said upper clip portion and being provided with a pointed end, said upper clip portion carrying at its free end opposite said bridge portion a rounded protector nose disposed in said plane of symmetry and having adjacent said protector nose an opening extending therethrough also in said plane of symmetry, the dimensions of said lower clip portion and said pin and of said upper clip portion from said bridge portion to said opening and also of said bridge portion being chosen such that the pointed end of said pin enters said opening when said upper clip portion is pressed onto said lower clip portion by deforming of said bridge portion, said pin having an end shape selected from a group consisting of a cone and pyramid and the length of the bridge portion being so dimensioned that, for closing the clip, said bridge portion is deformable in the plane of symmetry at two points at essentially right angles so that the closed clip assumes an essentially rectangular shape defined by said flexible bridge portion, said lower clip portion, said pin and said upper clip portion.

2. A clip according to claim 1, wherein said protector nose is rounded and bent upwardly from said upper clip portion.

3. A clip according to claim 2, wherein said pin, upon closing of said clip, is bent over toward said protector nose for locking said pin.

4. A clip according to claim 1, wherein the cross-section of said flexible bridge portion is smaller than that of said lower clip portion and said upper clip portion.

5. A clip according to claim 1, wherein the interface areas between said lower and upper clip portions and said flexible clip portion are formed as racking areas permitting deformation of said clip.

6. A clip according to claim 1, wherein said upper clip portion includes two control projections extending therefrom in the area adjacent said flexible bridge portion in opposite directions normal to said plane of symmetry.

7. A clip applicator for operating a clip as defined in claim 6, said clip applicator comprising a clip holder for grasping and holding the flexible bridge portion of said clip, a handle portion with an applicator tube which is movable by said handle portion axially with respect to said clip holder and a clip engaged thereby and which has an applicator head for engaging the flexible bridge portion of said clip when moved forwardly toward said clip bending said flexible bridge portion in such a manner that the lower clip portion and the upper clip portion are bent into an essentially parallel position in which the pointed end of said pin extends through the opening in the upper clip portion, said applicator head further having two opening studs and said clip holder including a stop bar for engaging said flexible bridge portion of said clip, said opening studs being adapted to engage said two control projections upon retraction of said applicator head for tilting said upper clip portion upwardly so as to extend essentially normal to said lower clip portion by bending said flexible bridge portion, said applicator tube when moved forwardly toward said clip bending said flexible bridge portion in such a manner that the lower clip portion and the upper clip portion are bent into an essentially parallel position in which the pointed end of said pin extends through the opening in the upper clip portion.

* * * * *